United States Patent [19]
Ware

[11] Patent Number: 6,140,467
[45] Date of Patent: *Oct. 31, 2000

[54] LIGAND FOR HERPES SIMPLEX VIRUS ENTRY MEDIATOR AND METHODS OF USE

[75] Inventor: Carl E. Ware, Solana Beach, Calif.

[73] Assignee: La Jolla Institute for Allergy and Immunology, La Jolla, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/898,234

[22] Filed: Jul. 30, 1997

Related U.S. Application Data

[60] Provisional application No. 60/051,964, Jul. 7, 1997.

[51] Int. Cl.⁷ ..................................................... C07K 14/47
[52] U.S. Cl. ............................................................... 530/350
[58] Field of Search ............................................. 530/350

[56] References Cited

FOREIGN PATENT DOCUMENTS

| WO 97/04658 A1 | 2/1997 | WIPO . | |
| 97/34911 | 9/1997 | WIPO | C07H 21/04 |
| 98/03648 | 1/1998 | WIPO | C12N 15/12 |

OTHER PUBLICATIONS

Harrop et al, Journal of Interferon and Cytokine Research 18(5): A–39, abstract 2.02, May 1998.
Hsu et al, Journal of Interferon and Cytokine Research 18(5): A–40, abstract 2.04, May 1998.
Mauri et al, Immunity 8:21–30, Jan. 1998.
Huang et al., "Anti–idiotypic antibodies mimicking glycoprotein D of herpes simplex virus identify a cellular protein required for virus spread from cell to cell and virus–induced polykaryocytosis", *Proceedings of the National Academy of Science USA,* Mar. 1996, vol. 93, pp. 1836–1840.
Montgomery et al., "Herpes Simplex Virus–1 Entry into Cells Mediated by a Novel Member of the TNF/NGF Receptor Family", *Cell,* Nov. 1, 1996, vol. 87, pp. 427–436.

*Primary Examiner*—Mary E. Mosher
*Attorney, Agent, or Firm*—Fish & Richardson PC

[57] ABSTRACT

A novel ligand (p30) for herpes virus entry mediator, HVEM, is provided. p30 is useful for modulating immune responses and in inhibiting infection by herpes virus. Methods for treating subjects with lymphoid cell disorders or those having or suspected of having a herpes virus infection, utilizing p30 of the invention, are also provided.

14 Claims, 10 Drawing Sheets

LIGAND FOR HERPES SIMPLEX VIRUS ENTRY MEDIATOR AND METHODS OF USE

CROSS-REFERENCE TO RELATED APPLICATION

This application claims priority under section 119 (e) (1) from U.S. Provisional Patent Application Ser. No. 60/051, 964, filed Jul. 7, 1997.

FIELD OF THE INVENTION

The invention relates generally to compounds and methods useful in regulating immune responses and viral infection and more specifically to a polypeptide useful in inhibiting infection by herpes simplex virus.

BACKGROUND OF THE INVENTION

Herpes simplex virus (HSV), types 1 and 2, causes recurrent infections that range in severity from benign to serious. HSV emerges from latency in neurons to infect the skin and other tissues in the presence of a competent cellular immune system. The D glycoprotein (gD) of HSV, a transmembrane protein located in the virion envelope, initiates infection by binding to cellular receptors [Spear et al. (1993) In, Viral Fusion Mechanisms. Ed. Bentz. CRC press, Boca Raton]. Recently, a cellular protein used by HSV for infection was identified and given the term HSV entry mediator (HVEM) [Montgomery et al. (1996) Cell 87:427]. HVEM is a transmembrane type 1 protein with a cysteine-rich extracellular domain that exhibits significant homology with receptors for tumor necrosis factor (TNF)-related cytokines [Smith et al. (1994) Cell 76:959; Ware et al. (1995) in, Pathways of Cytolysis. Eds. Griffiths and Tschopp. Springer-Verlag, Basel]. Many of the TNF superfamily members initiate a variety of cellular responses necessary to mount effective inflammatory and immune responses.

TNF is a type 2 transmembrane protein [Pennica et al. (1984) Nature 312:724] that is proteolyzed to form the secreted protein [Black et. al. (1997) Nature 385:729], whereas $LT\alpha$ lacks a transmembrane domain [Gray et. al. (1984) Nature 312:721] and is exclusively secreted as a homotrimer (in this form it was also known as $TNF\beta$). When expressed as a surface protein, $LT\alpha$ is associated with a 33 kDa protein [Androlewicz et al. (1992) J. Biol. Chem. 267:2542], termed $LT\beta$ [Browning et al. (1993) Cell 72:847], also a type 2 transmembrane glycoprotein, in heterotrimers of $\alpha1\beta2$ and $\alpha2\beta1$ subunit ratios [Androlewicz et al., cited supra; Browning et. al. (1996) J. Biol. Chem. 271:8618]. $LT\alpha$ and TNF both bind and signal through two receptors, the 55–60 kDa TNF receptor (TNFR60; CD120a or type 1) [Schall et al. (1990) Cell 61:361; Loetscher et al. (1990) Cell 61:351] and the 75–80 kDa TNFR (TNFR80; type 2 or CD120b) [Smith et al. (1990) Science 248:1019]. By contrast, the surface $LT\alpha1\beta2$ complex is recognized specifically by the $LT\beta$ receptor ($LT\beta R$) [Crowe et al. (1994) Science 264:707], which does not bind either $LT\alpha$ or TNF [Crowe et al. (1994) Science 264:707] whereas both TNFRs bind the $LT\alpha2\beta1$ heterotrimer [Crowe et al. (1994) Science 264:707; Browning et al. (1995) J. Immunol. 154:33].

Genetic deletions of $LT\alpha$ and $LT\beta$ genes in mice have revealed roles for these two genes in the development of lymph nodes and Peyer's patches [De Togni et al. (1994) Science 264:703; Banks et al. (1995) J. Immunol. 155:1685], and along with TNF and TNFR60, are also critical cytokines controlling the formation of germinal centers and immunoglobulin isotype switching (e.g., IgA production) during immune responses in adults [Matsumoto et al. (1996) Science 271:1289; Mariathasan et al. (1995) J. Inflammation 45:72]. Most studies have pointed towards the $LT\alpha1\beta2/LT\beta R$ as the critical cytokine-receptor system controlling these functions [Crowe et al. (1994) Science 264:707; Koni et al. (1997) Immunity 5:491; Ettinger et al. (1996) Proc. Natl. Acad. Sci. USA 93:13102; Rennert et al. (1996) J. Exp. Med. 184:1999].

SUMMARY OF THE INVENTION

The present invention is based on the identification of an endogenous polypeptide that functions as a ligand for HVEM, which previously was known only to bind HSV gD. This ligand, referred to as p30, is provided, as well as nucleic acid sequences encoding p30 and antibodies which bind to p30. The invention also includes methods for identifying compounds that modulate HSV infection, and methods for modulating lymphoid cell responses. The methods of the invention are useful for treating subjects with autoimmune diseases, lymphoid malignancies and HSV infection, for example.

In one embodiment the invention features an assay for identifying a compound which affects an HVEM-binding agent-mediated cellular response. Also within the invention is an assay for identifying a compound which affects an $LT\beta R$-p30-mediated cellular response.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present application, including definitions, will control. In addition, the materials, methods and examples described herein are illustrative only and not intended to be limiting.

Other features and advantages of the invention, e.g., therapy for a variety of human diseases, will be apparent from the following detailed description, from the drawings and from the claims.

DETAILED DESCRIPTION

Experiments involving inhibition of binding of a fusion protein containing the extracellular domain of the TNF receptor (TNFR) related polypeptide, HVEM, showed that the both malignant and normal human T-cells expressed a cell surface ligand for HVEM. Competitive inhibition experiments showed that the HVEM ligand has characteristics in common with LTαβ heterotrimers and LTα, but also has features that distinguish it from LTα1β2 and TNF. Thus, LTα2β1 could be a putative surface ligand recognized by HVEM, with the caveat that the HVEM binding site on LTα2β1 is not the same as TNFR60. Alternatively, HVEM might recognize a novel ligand. A biochemical approach was used to distinguish between these possibilities.

Figures 4A, 4B, 4C:
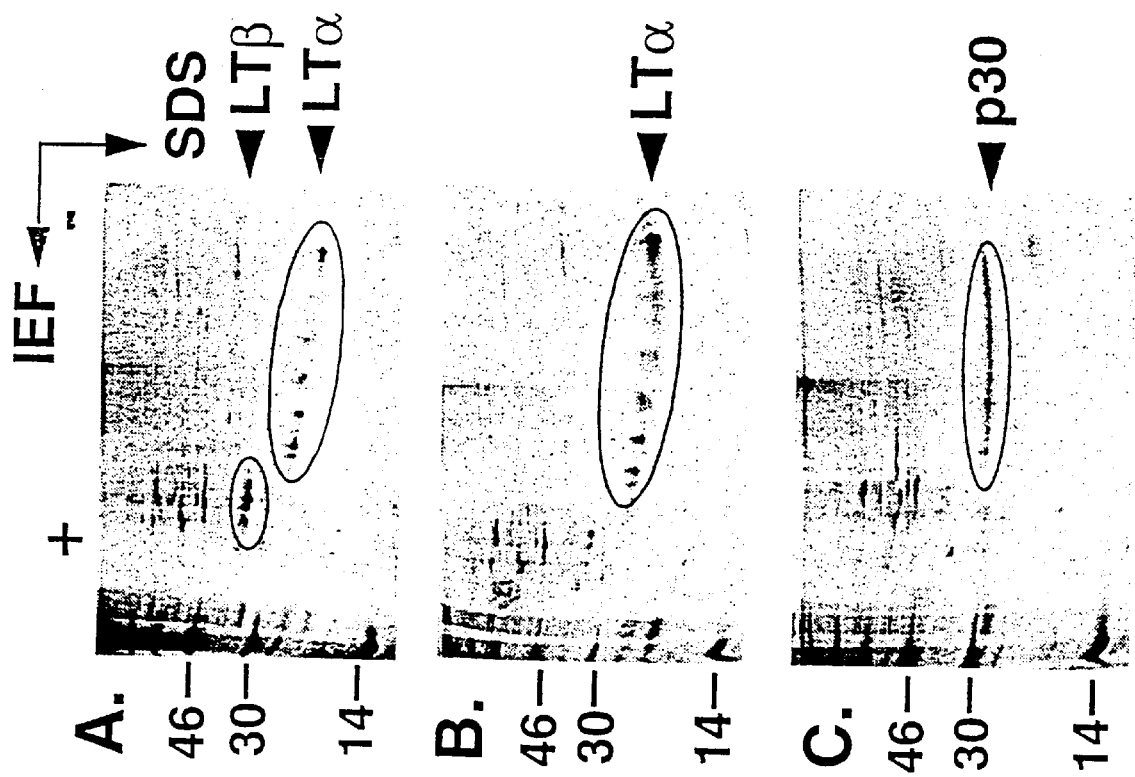
FIG. 4A is an autoradiogram obtained from a 2 dimensional isoelectric focusing/SDS-PAGE gel of a precipitate obtained by treating an extract of activated II-23.D7 cells with mLTβR:Fc fusion protein.
FIG. 4B is an autoradiogram obtained from a 2 dimensional isoelectric focusing/SDS-PAGE gel of a precipitate obtained by treating an extract of activated II-23.D7 cells with TNFR60:Fc fusion protein.
FIG. 4C is an autoradiogram obtained from a 2 dimensional isoelectric focusing/SDS-PAGE gel of a precipitate obtained by treating an extract of activated II-23.D7 cells with HVEM:Fc fusion protein.

Immunoprecipitation and sodium dodecyl sulfate polyacrylamide gel electrophoresis (SDS-PAGE) studies demonstrated the presence of a novel 30 kDa polypeptide ligand (p30) for HVEM on the surface of T cells that was antigenically distinct from both LTβ and LTα. Affinity chromatography purification and two-dimensional electrophoresis showed that p30 is also physically distinct from LTα and LTβ in that it has a molecular weight of 30 kDa and a pI of about 7–8.5 (FIG. 4C). In addition, these studies showed that p30 is also recognized by LTβR but not by TNFR.

Binding inhibition experiments demonstrated that soluble gD-1 (gD from HSV-1) and a mutant of gD-1, gD-1 (Δ290–299t) bind to HVEM but not to LTβR or TNFR60. This result suggests that gD-1 has co-evolved specifically for binding to HVEM, even though HVEM binds to ligands that are recognized by TNFR60 and LTβR. Furthermore, the findings indicate that gD-1 is a membrane-anchored virokine of the lymphotoxins and may modulate HVEM signaling activities during entry or egress of HSV from the infected cell.

In vitro cell culture studies showed that anti-HVEM antibody enhanced proliferation of both virgin and memory T cells. Similar experiments indicated that signaling through HVEM provided an activating stimulus to B cells and that a positive stimulus, without a counterbalancing negative stimulus via the TNFR, may be a unique property of the p30 HVEM ligand. These results indicate that the physiologic functions of the HVEM ligand is likely to be distinct from TNF and LTα1β2. The identification of a novel 30 kDa ligand for HVEM raises the possibility that this ligand, may be responsible for physiological responses previously ascribed to LTα or LTβ. The discoveries presented here provide a deeper understanding of the LT/TNF cytokine system and herpes virus that suggest new approaches for controlling these cytokines in disease processes.

Together, the results indicate that Fc fusion proteins containing HVEM or LTβR will modulate the action of LTα and the 30 kDa HVEM ligand, p30. Similarly, fusion protein HVEM could be used to identify specific inhibitors of the ligand receptor-complexes, such as monoclonal antibodies or peptides or small organic compounds. Inhibitors of p30 or LTα interactions with HVEM, or p30 interactions with LTβR, could be used to modulate diseases where unwanted lymphocyte proliferation occurs, including T and B lymphomas or leukemias, or in autoimmune diseases, such as rheumatoid arthritis, insulin-dependent diabetes mellitus, multiple sclerosis, systemic lupus erythematosus or myasthenia gravis.

Similarly, herpesvirus gD-1 could be used to inhibit immune reactions where LTα, p30 and HVEM signaling are implicated as effector molecules. LTα or soluble forms of the 30 kDa HVEM ligand (generated by deletion of its predicted cytoplasmic and transmembrane domains) may function as inhibitors of herpes virus infection and recrudesces by blocking the ability of herpes virus to enter a cellular target.

Like TNFRs, HVEM has a dual ligand specificity, binding to LTα and the distinct 30 kDa membrane bound ligand, p30. The LTα Tyr108Phe mutation destroys HVEM binding as it does for TNFR60 and TNFR80. The inability of TNFR60 to block HVEM binding to the surface 30 kDa form indicates that surface LTα2β1 is not an HVEM ligand.

Furthermore, the p30 differs from LTα because it is antigenically distinct and remains cell-associated, unlike LTα which is exclusively secreted. Thus, the HVEM binding protein (p30) is predicted to contain a stretch of hydrophobic residues forming a transmembrane domain arranged as a type-II transmembrane configuration similar to other proteins related to TNF. This does not exclude the possibility that p30 might also be modified in other ways (e.g., lipid modification) to allow attachment to the cell surface. Furthermore, this protein should share regions of sequence homology with LTα and LTβ and related cytokines that define this superfamily and contain a C-terminal extracellular domain of approximately 150–160 residues.

The inventors' findings also indicate that HVEM is a specific receptor for LTα, a property that clearly distinguishes it from the TNF binding receptors, TNFR60 and TNFR80. This property will allow an HVEM fusion protein or similar protein to antagonize LTα specifically without inhibiting TNF or LTα1β2 functions.

The present invention provides a substantially pure p30 polypeptide. The p30 polypeptide is characterized as having a predicted molecular weight of 30 kDa as determined by reducing SDS-PAGE and a pI in the range of about 7–8.5 (FIG. 4C). p30 exists in less than ten, preferably less than eight, more preferably less than six, (e.g. three, four or five) isomeric forms. The polypeptide is cell bound, i.e., is not secreted and, in its cell surface form, binds HVEM and LTβR.

The term "substantially pure", as used herein, refers to p30 polypeptide which is substantially free of other proteins, lipids, carbohydrates or other materials with which it is naturally associated. One skilled in the art can purify p30 using standard techniques for protein purification. [Protein Purification, Principles and Practice, second edition (1987) Scopes, Springer Verlag, N.Y.] The substantially pure polypeptide will yield a single major band of about 30 kDa on a reducing SDS-PAGE gel.

The invention includes a functional polypeptide, p30, and finctional fragments thereof. As used herein, the term "functional polypeptide" refers to a polypeptide which possesses a biological function or activity which is identified through a defined functional assay and which is associated with a particular biologic, morphologic, or phenotypic alteration in the cell. "Functional fragments" of the p30 polypeptide, includes fragments of p30 as long as the activity of p30 remains, e.g., modulation of cellular responses by binding to HVEM or LTβR or inhibiting binding of HSV to HVEM. Smaller peptides containing the biological activity of p30 are included in the invention. One of skill in the art can assay for functional activity of p30 by standard methods, e.g., viral plaque reduction assay or cell activation assays including cytokine production assays.

Minor modifications of the p30 primary amino acid sequence may result in proteins which have substantially equivalent activity as compared to the naturally occurring p30 polypeptide described herein. Such modifications may be deliberate, as by site-directed mutagenesis, or may be spontaneous. All of the polypeptides produced by these modifications are included herein as long as the biological activity of p30 is present, e.g., modulation of cellular responses by binding to HVEM and LTβR or inhibiting binding of HSV to HVEM. Further, deletion of one or more amino acids can also result in a modification of the structure of the resultant molecule without significantly altering its activity. This can lead to the development of a smaller active molecule which would have broader utility. For example, it is possible to remove amino or carboxy terminal amino acids which may not be required for p30 activity.

The p30 polypeptide of the invention also includes conservative variations of the polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention also provides isolated nucleic acid sequences encoding the p30 polypeptide of the invention.

The term "isolated" as used herein includes polynucleotides substantially free of other nucleic acids, proteins, lipids, carbohydrates or other materials with which it is naturally associated. Polynucleotide sequences of the invention include DNA, cDNA and RNA sequences which encode p30. It is understood that all polynucleotides encoding all or a portion of p30 are also included herein, as long as they encode a polypeptide with p30 activity. Such polynucleotides include naturally occurring, synthetic, and intentionally manipulated polynucleotides. For example, portions of the mRNA sequence may be altered due to alternate RNA splicing patterns or the use of alternate promoters for RNA transcription. As another example, p30 polynucleotide may be subjected to site-directed mutagenesis. The polynucleotide sequence for p30 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of p30 polypeptide encoded by the nucleotide sequence is functionally unchanged. In addition, the invention also includes a polynucleotide encoding a polypeptide having the biological activity of p30 and having at least one epitope for an antibody immunoreactive with p30 polypeptide.

The p30 nucleic acids of the invention include (a) the sequence that encode naturally occurring p30 and (b) any nucleotide sequences that hybridize to the complement of the sequences under highly stringent conditions, for example, hybridization to filter-bound DNA in 0.5 M $NaHPO_4$, 7% sodium dodecyl sulfate (SDS), 1 mM EDTA at 65° C., and washing in 0.1X SSC/0.1% SDS at 68° C. [Ausubel F. M. et al., eds., (1989) Current Protocols in Molecular Biology, Vol. I, Green Publishing Associates, Inc., and John Wiley & sons, Inc., New York] and encodes functionally equivalent gene products. The invention also includes degenerate variants of sequences (a) and (b).

The invention also includes nucleic acid molecules, preferably DNA molecules, that hybridize to, and are therefore the complements of the nucleotide sequences (a) and (b), in the preceding paragraph. Such hybridization conditions may be highly stringent, as described above or less highly stringent, such as moderately stringent conditions for example washing in 0.2 X SSC/0.1% SDS at 42° C. [Ausubel et al., cited supra]. In instances wherein the nucleic acid molecules are deoxyoligonucleotides ("oligos"), highly stringent conditions may refer, for example, to washing in 6X SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as p30 antisense molecules, useful, for example, in p30 regulation (for and/or as antisense primers in amplification reactions of p30 nucleic acid sequences). Still further, such molecules may be used as components of screening methods whereby, for example, the presence of a p30 gene may be detected.

In addition to the nucleotide sequences described above, full length cDNA or genomic sequences can be identified and readily isolated, without undue experimentation, by molecular biological techniques well known in the art. The invention encompasses these nucleic acid molecules.

DNA sequences of the invention can be obtained by several methods. For example, the DNA can be isolated using hybridization or computer-based techniques which are well known in the art. These include, but are not limited to: (a) hybridization of genomic or cDNA libraries with probes to detect homologous nucleotide sequences; (b) antibody screening of expression libraries to detect cloned DNA fragments with shared structural features; (c) polymerase chain reaction (PCR) on genomic DNA or cDNA using primers capable of annealing to the DNA sequence of interest; (d) computer searches of sequence databases for similar sequences; (e) differential screening of a subtracted DNA library; and (f) large scale genomic sequencing by expressed sequence tags (EST) of a T cell cDNA library.

Preferably the p30 polynucleotide of the invention is derived from a mammalian organism. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement [Wallace et al. (1981) Nucl. Acid Res., 9:879]. Alternatively, a subtractive library, is useful for elimination of non-specific cDNA clones.

When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form [Jay, et al., (1983) Nucl. Acid Res., 11:2325]. Appropriate oligonucleotide probes and primers can be constructed by "back-translating" the amino acid sequence of the p30 polypeptide obtained by N-terminal amino acid sequencing.

A cDNA expression library, such as lambda gt11, can be screened indirectly for p30 peptides having at least one epitope, using antibodies specific for p30. Such antibodies can be either polyclonally or monoclonally derived and used to detect expression product indicative of the presence of p30 cDNA.

Alterations in p30 nucleic acid include intragenic mutations (e.g., point mutation, nonsense (stop), missense, splice site and frameshift) and heterozygous or homozygous deletions. Detection of such alterations can be done by standard methods known to those of skill in the art including sequence analysis, Southern blot analysis, PCR based analyses (e.g., multiplex PCR, sequence tagged sites (STSs)) and in situ hybridization. Such proteins can be analyzed by standard SDS-PAGE and/or immunoprecipitation analysis and/or Western blot analysis, for example.

The invention also encompasses DNA vectors that contain any of the foregoing p30 coding sequences and/or their complements (i.e., antisense) and expression vectors that contain any of the foregoing p30 coding sequences. An expression vector is composed of or contains a nucleic acid in which a polynucleotide sequence encoding a peptide or polypeptide of the invention is operatively linked to a promoter or enhancer-promoter combination. A promoter is a trancriptional regulatory element composed of a region of a DNA molecule typically within 100 nucleotide pairs in front (upstream of) of the point at which transcription starts. Another transcriptional regulatory element is an enhancer. An enhancer provides specificity in terms of time, location and expression level. Unlike a promoter, an enhancer can function when located at variable distances from the transcription site, provided a promoter is present. An enhancer can also be located downstream of the transcription initiation site. A coding sequence of an expression vector is operatively linked to a transcription terminating region. To bring a coding sequence under control of a promoter, it is necessary to position the translation initiation site of the translational reading frame of the peptide or polypeptide between one and about fifty nucleotides downstream (3') of the promoter. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

Expression vectors and methods for their construction are known to those familiar with the art. Suitable vectors include plasmids, and viral vectors such as herpes viruses, retroviruses, canary pox viruses, adenoviruses and adeno-associated viruses, among others.

The invention includes suitable host cell lines transfected with expression vectors containing the p30 nucleic acid sequences described. Cells to be used for transfection include, but are not restricted to HEK293 cells of mammalian origin or Sf9 insect cells, for example, for expression of p30 in its various natural or engineered forms. Cells are transfected by a variety of methods commonly used in the art, for example, electroporation or calcium phosphate precipitation. Genes can also be introduced into the cells by transduction with viral vectors, e.g., retroviruses. Successfully transfected cell lines are selected by appropriate means familiar to those of average skill in the art, e.g., using tissue culture medium supplemented with a drug such as Geneticin™ (G418) or puromycin, for example, for which the relevant expression vector contains a resistance gene. Successfully transfected cell lines are screened for cell-surface expression of the p30 molecules by a variety of possible methods, e.g., flow cytometry analysis.

"Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used.

Antibodies that specifically recognize antigenic epitopes within the amino acid sequence of p30 are also encompassed by the invention. Such antibodies include but are not limited to polyclonal antibodies, monoclonal antibodies, human, humanized or chimeric antibodies, single chain antibodies, Fab fragments, F(ab')$_2$ fragments, and epitope-binding fragments of any of the above.

The antibodies of the invention can be used, for example, in the treatment of autoimmune diseases and lymphocytic malignancies. They can also be used to test for expression of p30 on a cell and may thus be utilized as part of a screening procedure to select an appropriate treatment for a particular subject. For example, if the tumor cells of a lymphoma or leukemia patient express p30, anti-p30 antibody or immunotoxin conjugates of anti-p30 antibody or immunotoxin conjugates of anti-p30 antibody may be used as therapy in that patient. Such antibodies may also be utilized in the screening assays of the invention.

For the production of antibodies of the invention, a host animal is immunized by injection with either a p30 polypeptide or with cells expressing the p30 polypeptide. Alternatively, peptides corresponding to p30-specific regions of these polypeptides may be used as immunogens. Such host animals may include but are not limited to rabbits, mice, and rats. Various adjuvants may be used to increase the immunological response, depending on the host species, including but not restricted to Freund's (complete and incomplete) adjuvant, mineral gels such as aluminum hydroxide, lysolecithin, pluronic polyols, polyanions, peptides, oil emulsions, BCG (bacille Calmette-Guerin) and *Corynebacterium parvum*. Polyclonal antibodies are heterogeneous populations of antibody molecules derived from the sera of the immunized animals.

In order to further enhance immunogenicity, the immunogen may be coupled to a carrier. Examples of such carriers are keyhole limpet hemocyanin (KLH) and bovine serum albumin (BSA). Other albumins such as ovalbumin, mouse serum albumin or rabbit serum albumin can also be used as carriers. Methods of coupling a peptide to a carrier are well known in the art and include the use of glutaraldehyde, carbodiimide and mmaleimidobenzoyl-N-hydroxysuccinimide ester.

The amount of antigen to be used can be determined readily by those with average skill in the art without undue experimentation. The antigen can be administered by a number of routes (e.g., subcutaneous, intramuscular, intradermal, intravenous and intraperitoneal). The production of polyclonal antibodies is monitored by sampling blood of the immunized animal at various time points after administration. When the desired level of antibody is obtained, the animal is bled and the serum is stored.

Monoclonal antibodies, which are homogeneous populations of antibodies to a particular antigen, may be obtained by any technique which provides for the production of antibody molecules by continuous cell lines in culture. These include, but are not limited to, the hybridoma technique [Kohler and Milstein (1975) Nature 256:495–497; U.S. Pat. No. 4,376,110; Howell and Lane (1988) Antibodies, A Laboratory Manual, Cold Spring Harbor Press, New York], the human B-cell hybridoma technique [Kosbor et al. (1983) Immunology Today 4:72; Cole et al. (1983) Proc. Natl. Acad. Sci. USA 80:2026], and the EBV-hybridoma technique [Cole et al. (1985), Monoclonal Antibodies And Cancer Therapy, Alan R. Liss, Inc.]. Such antibodies may be of any immunoglobulin class including IgG, IgM, IgE, IgA, IgD and any subclass thereof.

In addition, techniques developed for the production of "chimeric antibodies" can be used [Morrison et al. (1984) Proc. Natl. Acad. Sci. USA 81:6851; Neuberger et al. (1984) Nature 312:604; Takeda et al. (1985) Nature 314:452]. These involve splicing a portion of a gene encoding a mouse antibody of appropriate antigen specificity to a portion of a gene encoding a human antibody of appropriate biological activity. A chimeric antibody is a molecule in which different portions are derived from different animal species, such as those having a variable region derived from a murine monoclonal antibody and a human immunoglobulin constant region. Such chimeric antibodies could also be generated, for example, by immunizing mice containing the human genetic loci encoding IgH and K and λ light chain loci.

Alternatively, techniques described for the production of single chain antibodies [U.S. Pat. No. 4,946,778; Bird (1988) Science 242:423; Huston et al. (1988) Proc. Natl. Acad. Sci. USA 85:5879; and Ward et al. (1989) Nature 334:544] can be adapted to produce single chain antibodies against epitopes of p30. Single chain antibodies are formed by linking the heavy and light chain fragments of the Fv region via an amino acid bridge, resulting in a single chain polypeptide. They are conveniently produced by recombinant DNA techniques.

Antibody fragments which recognize specific epitopes may be generated by known techniques. For example, such fragments include but are not limited to the F(ab')$_2$ fragments which can be produced by pepsin digestion of the antibody molecule, and the Fab fragments which can be generated by reducing the disulfide bridges of the F(ab')$_2$ fragments. Alternatively, Fab expression libraries may be constructed [Huse et al. (1989) Science 246:1275] to allow rapid and easy identification of monoclonal Fab fragments with the desired specificity.

Methods for screening antibodies for binding specificity are well known in the art. These include, but are not restricted to, testing for: (a) binding to cells expressing cell surface p30; (b) lack of binding to cells not expressing p30; (c) binding to the p30 polypeptide; (d) lack of binding to polypeptides other than p30 (e.g., TNF, LTα, LTβ, Fas ligand, CD40 ligand or albumin; and (e) specific inhibition of binding to p30 by peptides corresponding to a region of interest within p30, e.g. a region involved in binding to HVEM or LTβR.

The invention features in vitro systems designed to identify compounds capable of modulating cellular responses mediated via either the HVEM or LTβR receptor polypeptides. "Cellular responses" refers herein to cell activation or cell internalization of HSV. These cellular responses are elicited by an interaction of (a) HVEM with p30, gD or LTα; or (b) LTβR with p30.

The term "ligand" refers to a polypeptide or a compound that binds to a receptor protein in a high affinity and specific manner to elicit a functional response. For example ligands of the invention include p30, gD or LTα. The term "receptor" refers herein to a polypeptide which, when bound by a ligand, induces a cellular response. Receptors of the invention include HVEM or LTβR. The term "binding agent" refers to a polypeptide or a compound that binds to a receptor or a ligand in a high affinity and specific manner and may or may not elicit a functional response. The test compound may be a defined, isolated and purified candidate compound (e.g., a synthetic small molecule), a member of a combinatorial library or it may be present in a biological sample such as a biological fluid, tissue extract, subcellular fraction or cellular lysate.

In one embodiment the invention features an assay for identifying a compound which affects an HVEM-binding agent-mediated cellular response. This assay involves: (a) incubating the compound with an HVEM polypeptide or a cell expressing an HVEM polypeptide, and an HVEM-binding agent, under conditions which allow the components to interact; and (b) determining the effect of the compound on the HVEM-binding agent-mediated cellular response. Also within the invention is an assay for identifying a compound which affects an LTβR-p30-mediated cellular response. This assay involves: a) incubating the compound with an LTβR polypeptide or a cell expressing an LTβR polypeptide, and with p30, under conditions which allow the components to interact; and (b) determining the effect of the compound on the LTβR-p30-mediated cellular response. In the assays of the invention compounds are screened for their ability to either modulate a cell activation mediated by interaction HVEM or LTβR with a ligand or to inhibit infection of susceptible cells by HSV.

The invention features cellular response assays. These cellular response assays measure either cell activation or cell infection by HSV.

Test compounds can be tested for their ability to modulate an response of cells expressing receptors (e.g., HVEM or LTβR) stimulated by ligands (e.g., p30, LTα or gD) and a suboptimal dose of a stimulus appropriate for the cells. The "responder" receptor expressing cells can be freshly obtained from a subject or they can be a cultured cell line. The cells can express endogenously encoded receptor or a receptor encoded by a transfected gene. The ligand may be added to the cellular response cultures in the form of an isolated polypeptide or by addition to the cultures of cells expressing the ligands. The ligand expressing cells may express an endogenous gene encoding the ligand or may express a transfected gene encoding the ligand. Furthermore the ligand may be expressed on the cell surface (p30 or gD) or be may be secreted (p30, gD or LTα). In order for p30 or gD to be secreted, the gene encoding it would need to have the region encoding the transmembrane domain deleted.

Cellular activation can be measured by, for example, cell proliferation, de novo expression of cell-surface activation markers, or soluble factor production.

In a preferred embodiment, the cells are lymphocytes. In the case of T cells, the receptor (HVEM or LTβR) expressing responder T cells can be cultured in the presence of the test compound, the ligand and a suboptimal dose of a T cell activator, e.g., anti-CD3 antibody, a lectin such as phytohemoglutinin (PHA) or a superantigen such as staphylococcal enterotoxin C (SEC). Controls will be cultures containing: (a) T cells alone; (b) T cells with T cell activator, with ligand and without test compound; (c) T cells with T cell activator, without ligand and without test compound; (d) T cells with T cell activator, without ligand and with test compound, (e) T cells without T cell activator, with ligand and without test compound; (f) T cells without T cell activator, without ligand and without test compound and (g) T cells without T cell activator, without ligand and with test compound. T-cell activation can be measured in terms of T cell proliferation by incorporation of $^3$H-thymidine (see Example 5), induction of activation markers such as CD69 or CD25, or production of cytokines such as interleukin-2 (IL-2), interleukin-4 (IL-4) or interferon-γ (IFNγ).

In the case of B lymphocytes similar response assays can be carried out. The B cell activators may be mitogens such as poke weed mitogen, staphylococcal protein A or anti-immunoglobulin. Cell activation cell can be measured by cell proliferation (again by $^3$H-thymidine incorporation) or Ig secretion. Alternatively, the survival of B cells in nutritionally suboptimal medium may be measured (see Example 5).

The ability of a test compound to inhibit lymphocyte activation would be an indication that such a compound may be useful in the treatment of an autoimmune disease largely involving T-cells (rheumatoid arthritis, insulin dependent diabetes mellitus and multiple sclerosis, for example) or T and B cells (systemic lupus erythematosus and myasthenia gravis, for example). The ability of a test compound to stimulate lymphocyte activation would be an indication that such a compound may be useful in stimulating immune responses in subjects with infectious diseases, or in which the subject is immunosuppressed as, for example, in patients undergoing chemotherapy or radiation therapy for cancer or in patients with AIDS.

In assays for test compounds that prevent HSV infection, the test compounds can be added to cultures of HSV susceptible cells and HSV. Permissive cell lines for virus infection include human dermal fibroblasts, peripheral blood lymphocytes treated with agents that cause activation (e.g., anti-CD3 antibody, or phytohemagglutinin), and transformed cell lines (e.g., Held cells). Virus production can be measured by any number of methods known by those skilled in the art including viral plaque assays, production of specific virus proteins measured by an ELISA or use of recombinant virus that contains an indicator gene product like β-galactosidase, an enzyme easily detectible by colorimetric assays [Montgomery et al., cited supra].

The ability of a test compound to inhibit cell infection by HSV would be an indication that such a compound may be useful in the treatment of a subject with an HSV infection.

In order to test whether compounds which affect cellular responses function by binding either member of the relevant receptor-ligand pair, they can be tested for their ability to bind to soluble forms of the receptor or ligand by assays well known in the art, for example, ELISAs, Western blotting or radioimmunoassays. Furthermore, to test whether binding of a test compound to either the receptor or the ligand results in inhibition of their binding to each other, the test compound can be tested for its capacity to inhibit binding of soluble forms of the receptor and the ligand. Examples of these assays are competitive ELISAs, competitive Western blotting and competitive radioimmunoassays.

Peptides and polypeptides used in the screening assays of the invention may be obtained by a variety of means. Smaller peptides (less than 50 amino acids long) may be conveniently synthesized by standard chemical methods. Some polypeptides (e.g. antibodies) may be purchased from commercial sources. Where otherwise unavailable, antibodies can be generated as described supra. Detectably labeled antibodies either can be purchased from commercial sources or are readily prepared by those of ordinary skill in the art.

Polypeptides such as HVEM, LTβR, p30, gD or LTα may be purified from biological sources by methods well-known to those skilled in the art [Protein Purification, Principles and Practice, second edition (1987) Scopes, Springer Verlag, New York]. They may also be produced in their naturally occurring, truncated, fusion or chimeric protein forms by recombinant DNA technology using techniques well known in the art. These methods include, for example, in vitro recombinant DNA techniques, synthetic techniques, and in vivo genetic recombination. See, for example, the techniques described in Sambrook et al. (1989) Molecular Cloning, A Laboratory Manual, Cold Spring Harbor Press, New York; and Ausubel et al., cited supra. Alternatively, RNA encoding the proteins may be chemically synthesized. See, for example, the techniques described in Oligonucleotide Synthesis, (1984) Gait, M. J. ed., IRL Press, Oxford, which is incorporated by reference herein in its entirety.

A variety of host-expression vector systems may be utilized to express the nucleotide sequences. Where the peptide or polypeptide is soluble, it can be recovered from: (a) the culture, i.e., from the host cell in cases where the peptide or polypeptide is not secreted or (b) from the culture medium in cases where the peptide or polypeptide is secreted by the cells. The expression systems also encompass engineered host cells that express the polypeptide in situ, i.e., anchored in the cell membrane. Purification or enrichment of the polypeptide from such an expression system can be accomplished using appropriate detergents and lipid micelles and methods well known to those skilled in the art. Alternatively, such engineered host cells themselves may be used in situations where it is important not only to retain the structural and functional characteristics of the protein, but also to assess biological activity.

The expression systems that may be used for purposes of the invention include but are not limited to microorganisms such as bacteria (for example, E. coli and B. subtilis) transformed with recombinant bacteriophage DNA, plasmid DNA or cosmid DNA expression vectors containing the nucleotide sequences; yeast transformed with recombinant yeast expression vectors; insect cells infected with recombinant viral expression vectors (baculovirus); plant cell systems infected with recombinant viral expression vectors (e.g., cauliflower mosaic virus, CaMV; tobacco mosaic virus, TMV) or transformed with recombinant plasmid expression vectors; or mammalian cells (e.g., COS, CHO, BHK, 293, 3T3) harboring recombinant expression constructs containing promoters derived from the genome of mammalian cells (e.g. metallothionein promoter) or from mammalian viruses.

In bacterial systems, a number of expression vectors may be advantageously selected depending upon the use intended for the gene product being expressed. For example, when a large quantity of such a protein is to be produced, e.g. for raising antibodies to the protein, vectors which direct the expression of high levels of fusion protein products that are readily purified may be desirable. Such vectors include, but are not limited to, the E. coli expression vector pUR278 [Ruther et al. (1983) EMBO J. 2:1791], in which the coding sequence may be ligated individually into the vector in frame with the lacZ coding region so that a fusion protein is produced; pIN vectors [Inouye & Inouye (1985) Nucleic Acids Res. 13:3101; Van Heeke & Schuster (1989) J. Biol. Chem. 264:5503]; and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety. It is understood that the polypeptides used for the screening assays can be either the naturally occuring forms of the polypeptides or fusion proteins containing the polypeptides. The irrelevant part of the fusion protein can be, for example, the Fc portion of immunoglobulin G, hexahistidine or GST.

In mammalian host cells, a number of viral-based expression systems may be utilized. In cases where an adenovirus is used as an expression vector, the nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the gene product in infected hosts [e.g., See Logan & Shenk (1984) Proc. Natl. Acad. Sci. USA 81:3655]. Specific initiation signals may also be required for efficient translation of inserted nucleotide sequences. These signals include the ATG initiation codon and adjacent sequences. In cases where an entire gene or cDNA, including its own initiation codon and adjacent sequences, is inserted into the appropriate expression vector, no additional translational control signals may be needed. However, in cases where only a portion of the coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. [Bittner et al. (1987) Methods in Enzymol. 153:516].

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Appropriate cell lines or host systems can be chosen to ensure the correct modification and processing of the foreign protein expressed. Mammalian host cells include but are not limited to CHO, VERO, BHK, Held, COS, MDCK, 293, 3T3, and WI38.

For long-term, high-yield production of recombinant proteins, stable expression is preferred. For example, cell lines which stably express the sequences described above may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched medium, and then are switched to a selective medium. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the gene product. Such engineered cell lines may be particularly useful in screening and evaluation of compounds that affect the endogenous activity of the gene product.

A fusion protein may be readily purified by utilizing an antibody or a moiety that specifically binds to the fusion protein being expressed. For example, a system described by Janknecht et al. [(1991) Proc. Natl. Acad. Sci. USA 88:8972] allows for the ready purification of non-denatured fusion proteins expressed in human cell lines. In this system, the gene of interest is subcloned into a vaccinia recombination plasmid such that the gene's open reading frame is translationally fused to an arnino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers. If desired, the histidine tag can be selectively cleaved with an appropriate enzyme.

Chimeric proteins may also be derived by methods known to those in the art. These involve splicing a portion of a gene encoding a given protein to one or more portions derived from one or more genes encoding different proteins. A chimeric polypeptide is a molecule in which different portions are derived from different proteins. For example, a chimeric protein may contain a domain of HVEM and another domain of LTβR.

The invention provides methods for modulating an HVEM-mediated cellular response by contacting a cell expressing the receptor polypeptide, HVEM, with an HVEM binding agent. Alternatively, an HVEM-mediated cellular response is modulated by contacting a ligand for HVEM with a ligand binding agent. Such ligands include p30, LTα or gD. In general p30 is expressed on the surface of a cell, LTα is secreted and gD is expressed on an HSV virion or on the surface of an HSV-infected cell. The phrase "cellular responses" refers again herein to cell activation or to internalization of HSV by the cell. The invention also features methods for modulating LTβR-mediated cellular responses by contacting a cell expressing LTβR or a cell expressing the LTβR ligand, p30, with a binding agent that binds either to HVEM or the p30.

As used herein, the term "contacting" means exposing the receptor or the ligand to the binding agent, in a receptor-modulating effective amount, so that the binding agent can effectively modulate the cellular response initiated by interaction of the ligand with the receptor. Modulation can result in inhibition or activation of the cellular response. These alternative properties of a particular binding agent for a particular receptor-ligand pair can be tested for in advance using the screening assays described.

With respect to receptor binding agents, HVEM binding agents include soluble gD, soluble p30 or a peptide fragment of LTα, preferably a peptide fragment that contains the amino acid Tyr at a position corresponding to position 108 from the N-terminus of naturally occuring LTα. An LTβR binding agent is soluble p30.

With respect to ligand binding agents, p30 binding agents include soluble HVEM, soluble LTβR or antibody that binds specifically to p30. An LTα binding agent is soluble HVEM.

Contacting may be in vitro, for example, by adding a binding agent to a culture of cells expressing HVEM or LTβR, e.g., lymphocytes, undergoing activation by HVEM ligands (p30, LTα or gD) or the LTβR ligand, p30. Binding agents may also be added, for example, to a culture of HVEM expressing cells exposed to gD on the surface of HSV virions or on the surface of HSV infected cells. The ability of the binding agent to modulate these cellular responses could be tested for in advance using the screening methods described. The binding agent may be added as an isolated polypeptide or as cells transfected with an expressing vector containing a binding agent encoding nucleic acid molecule. In these in vitro methods, a "receptor-modulating effective amount" of binding agent, is the amount required to modulate cell activation or HSV infection by greater than 20%, preferably greater than 50%, more preferably greater than 80% and most preferably greater than 95%.

Contacting may be in vivo in a subject. The subject may be a mammal, preferably a human, with an autoimmune disease such as rheumatoid arthritis, insulin dependent diabetes mellitus, multiple sclerosis, systemic lupus erythematosus or myasthenia gravis, a lymphoid (T or B cell) malignancy, an HSV infection, an infection with an organism other than HSV or immunosuppression. Inhibition of a HVEM-p30 or a LTβR-p30 mediated cellular response could be advantageous in patients with autoimmune diseases or lymphoid malignancies in that it could prevent T cell proliferation (as in rheumatoid arthritis, insulin dependent diabetes mellitus, multiple sclerosis, systemic lupus erythematosus, myasthenia gravis and T cell malignancies) and B cell proliferation (as in systemic lupus erythematosus, myasthenia gravis and B cell malignancies). Inhibition of an HVEM-gD mediated cellular response (i.e., HSV internalization) could be therapeutic for subjects with an HSV infection in that it would prevent viral spread mediated by internalization of gD-expressing HSV virions present in the extracellular space or from HSV-infected cells expressing gD on their surface. Stimulation of an HVEM-p30 or a LTβR-p30 mediated cellular response would be useful in treating subjects with an infection other than HSV or immunosuppressed subjects ( e.g., patients undergoing radiation and/or chemotherapy for cancer, other than lymphoid malignancies) or AIDS patients in that both T and B cell proliferation would be stimulated. Naturally, one would avoid using binding agents that stimulate an HVEM-p30 mediated cellular response in a subject with an HSV infection in that such an agent might also enhance an HVEM-gD cellular response and, thereby, the spread of HSV virus. However, this activity in the relevant binding agent could be tested for in advance using the screening assays described supra. Similarly, these stimulatory binding agents would not be used in lymphoid malignancies as they could promote growth of the tumor cells.

The binding agents to be used for in vivo modulation of cellular responses include the naturally occuring forms of HVEM, LTβR, p30, gD and LTα. These will be produced by the methods described supra. Also included are antibodies to p30. Peptides derived from LTα and which modulate the HVEM-LTα interaction will also be used. The peptides will contain less than 205, preferably less than 100, more preferably less than 50 and most preferably less than 20 amino acids. For example, they may contain five, eight, twelve, fifteen or eighteen amino acids. The peptides will preferably contain the residue Tyr, or a conservative replacement thereof, at a position corresponding to amino acid residue 108 from the N-terminus of naturally occuring LTα.

Also included as binding agents are peptidomimetics of the peptides described supra. Peptidomimetic compounds are synthetic compounds having a three-dimensional structure (i.e. a "peptide motif") based upon the three-dimensional structure of a selected peptide. The peptide motif provides the peptidomimetic compound with the activity of modulating cellular responses that is the same or greater than the activity of the peptide from which the peptidomimetic was derived. Peptidomimetic compounds can have additional characteristics that enhance their therapeutic application such as greater affinity and/or avidity and prolonged biological half-life. The peptidomimetics of the invention typically have a backbone that is partially or completely non-peptide, but with side groups identical to the side groups of the amino acid residues that occur in the peptide on which the peptidomimetic is based. Several types of chemical bonds, e.g. ester, thioester, thioamide, retroamide, reduced carbonyl, dimethylene and ketomethylene bonds, are known in the art to be generally useful substitutes for peptide bonds in the construction of protease-resistant peptidomimetics.

Polypeptide and peptide binding agents may be modified by the addition at either or both the amino- and carboxy-terminal ends, of a blocking agent in order to facilitate survival of the relevant polypeptide or peptide in vivo. This can be useful in those situations in which the peptide termini tend to be degraded ("nibbled") by proteases. Such blocking agents can include, without limitation, additional related or unrelated peptide sequences that can be attached to the amino and/or carboxy terminal residues of the polypeptide or peptide to be administered. This can be done either chemically during the synthesis of the peptide or polypeptide or by recombinant DNA technology. Alternatively, blocking agents such as pyroglutamic acid or other molecules known to those of average skill in the art may be attached to the amino and/or carboxy terminal residues, or the amino group at the amino terminus or carboxyl group at the carboxy terminus replaced with a different moiety. Likewise, the binding agents can be covalently or noncovalently coupled to pharmaceutically acceptable "carrier" proteins prior to administration.

In vivo delivery involves administering to a subject either the binding agent itself, a nucleic acid encoding the binding agent, an expression vector encoding the binding agent, or cells transfected or transduced with the vector.

Binding agents may be delivered to a cell of a mammal using techniques substantially the same as those described infra for delivery to human subjects. Examples of appropriate mammals include but are not restricted to humans, non-human primates, horses, cattle, sheep, dogs, cats, mice, rats, guinea pigs, hamsters, rabbits and goats.

A binding agent may be delivered to cells of a patient in its unmodified state, dissolved in an appropriate physiological solution, e.g. physiological saline. Naturally, it is desirable that these peptides be selectively targeted to relevant tissues and cell types. This can be achieved by contacting the peptides directly with the affected organ or tissue, e.g., by localized injection or implantation. Thus, in autoimmune diseases such as rheumatoid arthritis or insulin-dependent diabetes mellitus, the peptides could be introduced directly into affected joints or the pancreas, respectively, or, preferably, into draining lymphoid tissue in which the active autoimmune response occurs.

Alternatively, the binding agents may be delivered in liposomes into which have been incorporated ligands for receptors on relevant cells (e.g., T cells or B cells) or antibodies to cell-surface markers expressed by these cells. Thus an antibody specific for the CD4 T cell surface marker may direct liposomes containing both the anti-CD4 antibody and the relevant binding agent to a CD4+T cell. This approach could be used in both autoimmune diseases and HSV infection. In autoimmune diseases in which the T cell receptor (TCR) expressed by a dominant pathogenic T-cell clone has been defined, an antibody specific for the relevant TCR component (e.g. Vβ) may be used. The latter methodology would represent an ideal form of immunotherapy in which pathogenic effector cells are specifically targeted for inhibition while the immune system as a whole and the cells of the target organ remain uncompromised.

In lymphoma or leukemia patients, anti-proliferative binding agents are preferably directed to cancer cells. The peptides could, for example, be injected directly into the tissues surrounding the lymphoma tumor site after surgery to remove the tumor, in order to inhibit growth of residual tumor cells. Instead of surgery, the tumor could be treated by in situ injection of the binding agent into the tumor. The liposome methodology described supra, could also be exploited. In this case antibodies specific for tumor-specific antigens (TSA) or tumor-associated antigens (TAA) would be exploited.

It is well known in the medical arts that dosages for any one patient depend on many factors, as well as the particular compound to be administered, the time and route of administration and other drugs being administered concurrently. Dosages for the binding agents of the invention will vary, but can be, when administered intravenously, approximately 0.01 mg to 10 mg/ml blood volume. Routes and doses of administration are well known to skilled pharmacologists and physicians. Routes, in addition to those described supra, include, but are not restricted to: intraperitoneal, intramuscular, intrapulmonary, transmucosal, subcutaneous and intravenous.

An in vivo gene therapy approach requires delivery of a genetic construct directly into the patient, preferably targeting it to the cells or tissue of interest. For example, after surgical removal of a primary tumor, residual cells may be targeted by treating the vicinity of the tumor with a composition containing a retroviral vector encoding an anti-proliferative binding agent. Alternatively, instead of surgery, the primary tumor could be treated by in situ injection of the vector directly into the tumor. Malignant cells distal to the primary tumor site may be reached by delivering the vector intravenously. Similarly, targeting of tissues under autoimmune attack may be achieved by direct injection of vectors. Targeting of tumor cells or activated lymphocytes, for example, can be accomplished by the use of a retrovirus, which stably transfects primarily proliferating cells.

Tissue specific targeting may also be achieved by the use of a molecular conjugate composed of a plasmid or other vector attached to poly-L-lysine by electrostatic or covalent forces. Poly-L-lysine binds to a ligand that can bind to a receptor on tumor cells [Cristiano et al. (1995) J. Mol. Med 73:479]. Similarly, tumor and cell specific antibodies of the type described supra can be bound to vectors and thereby target them to lymphoid tumors or cells such as T-lymphocytes. The latter would be useful in autoimmune diseases and HSV infection. A promoter inducing relatively tumor-specific expression can be used to achieve a further level of targeting. Tissue-specific promoters for use in autoimmune or transplant patients include, for example, the inducible IL-2 [Thompson et al. (1992) Mol. Cell. Biol. 12: 1043], IL-4 [Todd et al. (1993) J. Exp. Med. 177:1663] and gamma-interferon [Penix et al. (1993) J. Exp. Med. 178:483] T-cell targeting promoters. Such inducible promoters would have an invaluable additional advantage in that expression would occur selectively in activated T-cells. Included in this population of activated T-cells are the effector cells that an ideal immuno-therapeutic modality would selectively inhibit in autoimmune patients.

Vectors can also be delivered by incorporation into liposomes or other delivery vehicles either alone or co-incorporated with cell specific antibodies, as described supra.

Where the relevant binding agent is normally bound to the cell membrane (HVEM, LTβR, p30 or gD), the region of the nucleic acid encoding the transmembrane domain of binding agent will be deleted from the nucleic acid contained in the expression vector.

DNA or transfected cells may be administered in a pharmaceutically acceptable carrier. Pharmaceutically acceptable carriers are biologically compatible vehicles which are suitable for administration to a human, e.g., physiological saline. A therapeutically effective amount is an amount of the DNA of the invention which is capable of producing a medically desirable result in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for intravenous administration of DNA is from approximately $10^6$ to $10^{12}$ copies of the DNA molecule. This dose can be repeatedly administered, as needed.

The following examples are meant to illustrate the invention and not to limit it.

EXAMPLES

Materials

Construction, expression and purification of the bivalent chimeric proteins formed with the Fc region of human IgG1 and the ligand binding domains of Fas:Fc [Brunner et al. (1995) Nature 373:441], TNFR60 [Crowe et al. (1994) J. Immunol. Methods 168:79] and human LTβR:Fc [Crowe et al. (1994) Science 264:707] have been previously described. The extracellular region of HVEM was generated by PCR using Taq DNA polymerase amplified sequences from pBEC10 DNA encoding 1-K184 using the forward primer 5'-CGGAGATCTGAGTTCATCCTGCTAGCTGG-3' (SEQ ID NO:1) and reverse primer 5'-ATAGGATCCCTTGGTCTGGTGCTGACATTCC-3' (SEQ ID NO:2). The amplified HVEM product was ligated in-frame into the baculovirus vector pVL1392 (Pharmingen) containing the human Fc IgG1. A similar construct of HVEM:Fc with Fc region from rabbit IgG1 was produced in CHO cells, purified and used as an immunogen to produce rabbit anti-HVEM antibody. LTβR:Fc was constructed from a mouse LTβR (mLTβR) DNA fragment that encodes amino acid residues 1-Met221 of the extracellular domain [Force et al. (1996) J. Immunol. 1995.1 155:5280] by PCR using Taq DNA polymerase with forward primer 5'-GACGTCAGATCTTCCCACCTTTCCTCCTA-3' (SEQ ID NO:3) and reverse primer 5'-GAACAGAGATCTCATTGCTCCTGGCTCTG-3' (SEQ ID NO:4). LTα and LTαTyr108Phe were produced in insect cells using recombinant baculovirus as described [Crowe et al. (1994) J. Immunol. Methods 168:79]. Recombinant soluble LTα1β2 [Browning et al. (1996), cited supra], TNF [Browning and Ribolini (1989) J. Immunol. 143:1859], and monoclonal antibodies to LTα (BF7), and LTβ (C37, B9 and B27) [Browning et al. (1995), cited supra] were generous gifts from Jeffrey Browning (Biogen, Inc.). The immunoprecipitating anti-LTα antibody (clone 9B9) was from Boehringer Mannheim. Anti-CD3 (OKT3) was produced in ascites in BALB/c mice and used at 1 μg/ml protein. Purified recombinant HSV gD-1 proteins and mutants were produced in baculovirus as previously described in detail (Nicola et al. (1996) J. Virol. 6:3815]. FITC-anti-CD4 and CD8 antibodies were obtained from Becton-Dickenson.

Example 1

Expression of an HVEM Ligand on T Cells

Methods

Binding of HVEM to II.23.D7 cells The II-23.D7 cell line is a human CD4+T cell hybridoma [Ware et al (1986) Lymphokine Res. 5:313] and is maintained in RPMI1640 medium with 10% fetal bovine serum (FBS) and antibiotics. II-23.D7 cells were activated for 4 hours at 37° C. with phorbol myristate acetate (PMA) (100 ng/ml), or PMA (100 ng/ml) and ionomycin (1 μg/ml). The cells were washed and incubated for 30 minutes at 4° C. in Hanks Balance Salt Solution (HBSS) (supplemented with 10% bovine calf serum and 0.1% NaN$_3$) containing HVEM:Fc, LTβR:Fc or human IgG at 5 μg/ml, and then stained with goat anti-human IgG conjugated with phycoerythrin (anti-huIg-PE). Stained cells were analyzed by flow cytometry (FACSCaliber, Becton-Dickenson). Each histogram represents $10^4$ events. Binding of HVEM to normal human T cell Peripheral blood mononuclear cells obtained from normal donors by Ficoll-Hypaque were activated with anti-CD3 antibody for 5 days in medium with IL-2. Cells were restimulated with PMA or PMA and ionomycin for 4 hours and then dual stained with FITC-CD4 or FITC-CD8 and HVEM:Fc detected with anti-huIgG-PE as described above. FITC fluorescence with compensation was used to gate on CD4 and CD8 T cell subpopulations. Receptor binding Receptor binding was determined by incubating graded concentrations of HVEM:Fc or control IgG with activated II-23.D7 cells as described above. Receptor binding was determined by calculating the fluorescence intensity=(mean fluorescent channel)(% positive fluorescent events), where a positive event has a fluorescence value>98% of the value for normal IgG. Specific fluorescence intensity represents the fluorescence intensity after subtraction of the value for control IgG.

Results

Figure 1A:
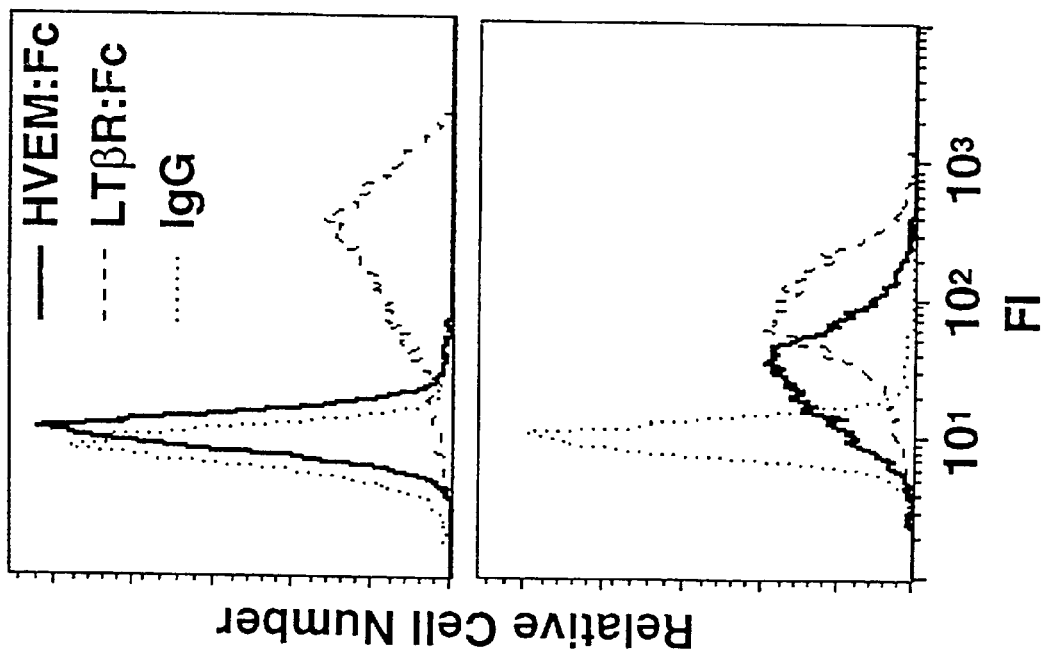
FIG. 1A is a pair of flow cytometric histograms showing the binding of HVEM:Fc fusion protein to II-23.D7 cells after activation with PMA (upper histogram) or PMA and ionomycin (lower histogram).
Figure 1B:
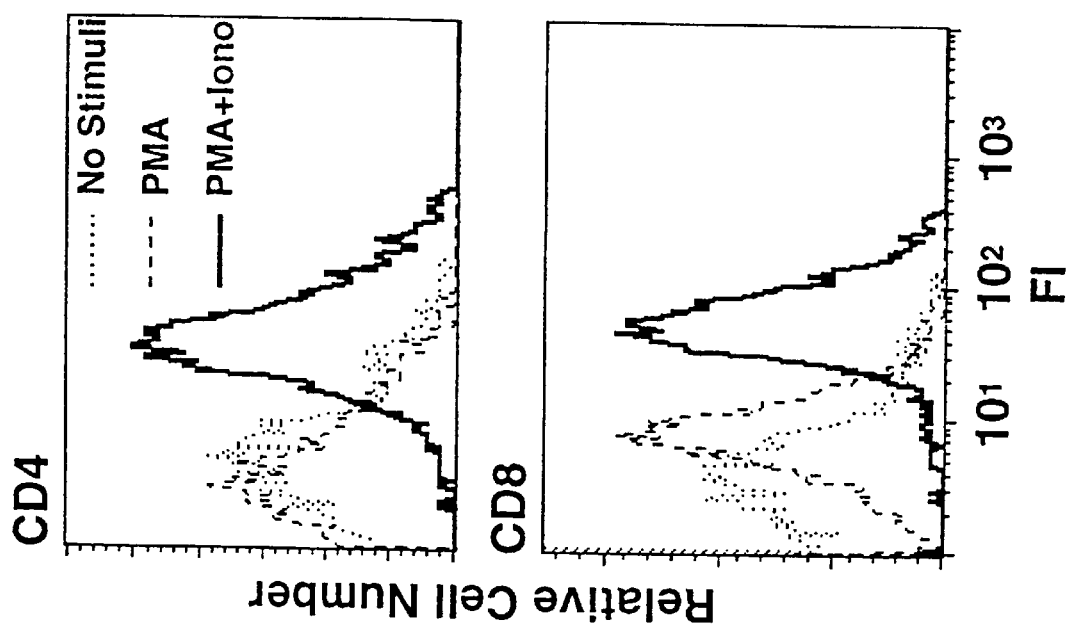
FIG. 1B is a pair of flow cytometric histograms showing the binding of HVEM:Fc fusion protein to normal human CD4+(upper histogram) and CD8+(lower histogram) T cells.
Figure 1C:
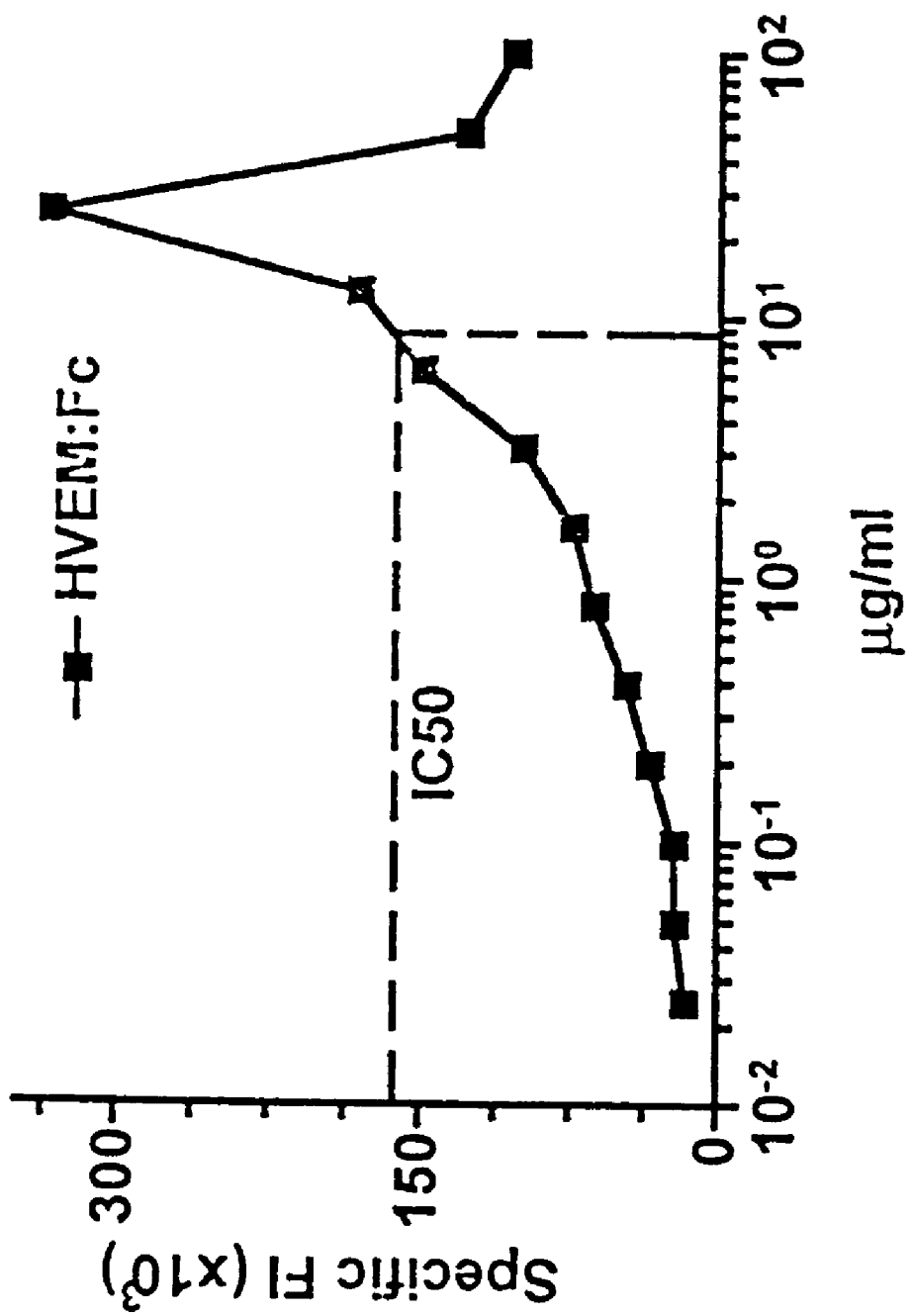
FIG. 1C is a line graph showing saturation binding of HVEM:Fc fusion protein to activated II-23.D7 cells.

In order to test for a putative ligand for HVEM, a fusion protein containing the extracellular domain of HVEM and the Fc region of human IgG (HVEM:Fc) was constructed. Specific binding of HVEM:Fc bound to the human CD4+T cell hybridoma, II.23.D7 [Ware et al. (1986), cited supra] after activation with the calcium ionophore, ionomycin, and PMA, but not PMA alone was detected by flow cytometry (FIG. 1A). Specific HVEM:Fc binding was also detected on T lymphocytes derived from human peripheral blood (FIG. 1B). These findings indicated that the both malignant and normal human T-cells expressed a cell surface ligand for HVEM. Half-maximal binding of HVEM:Fc to II.23.D7 cells was achieved at ~20 nM (FIG. 1C). The II.23.D7 cell line is also induced by PMA to express LTα and β and TNF [Ware et al. (1992) J. Immunol. 149:3881].

Example 2

Binding Characteristics of the HVEM Ligand

Methods

Competition of binding by LTβR:Fc Activated II-23.D7 cells (PMA and ionomycin as described in Example 1) were pre-incubated with LTβR:Fc or TNFR60:Fc (100 μg/ml) for 30 minutes at 4° C. HVEM:Fc-rabbit (2 μg/ml) was then added, incubated for 30 minutes and the cells stained with goat anti-rabbit IgG-PE to detect HVEM:Fc-rabbit. Rabbit IgG was used to determine background staining. Binding of HVEM:Fc to activated II-23.D7 cells was competed with graded concentrations of LTβR:Fc, TNFR60, Fas:Fc, or IgG as described above. Competition of binding by LTα homotrimer II-23.D7 cells were activated and HVEM:Fc was preincubated with recombinant LTα or LTα1β2 for 30 minutes at 4° C. The mixture was added to activated II-23.D7 cells and then stained with anti-huIgG-PE. Fluorescence staining with HVEM:Fc+LTα was equal to background with normal IgG.

Results

Figure 2A:
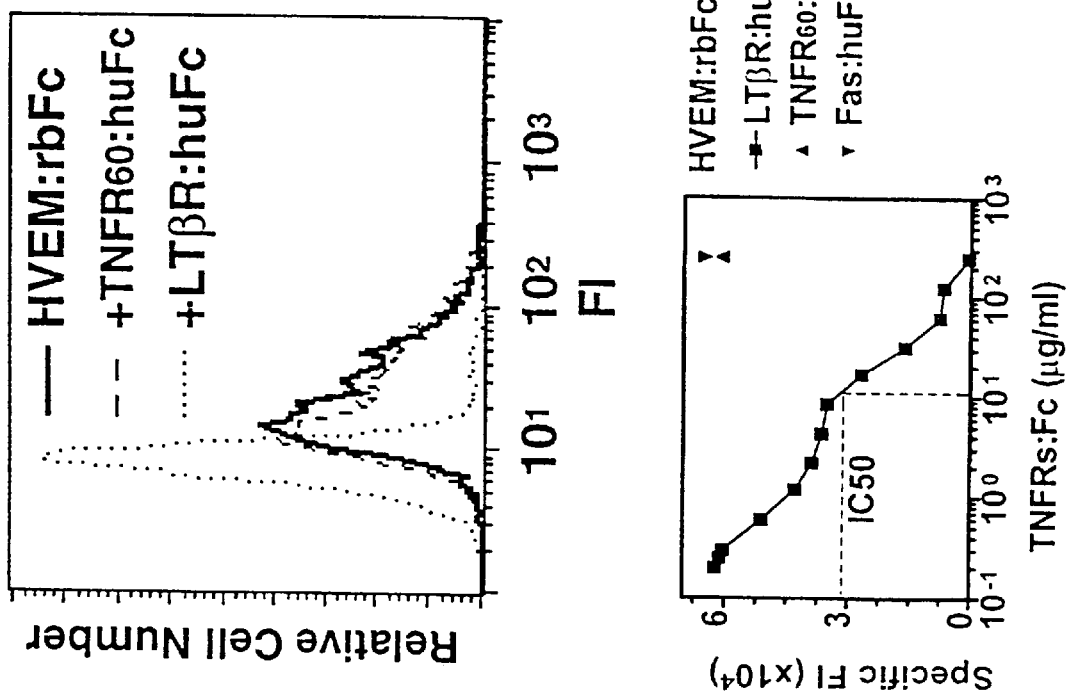
FIG. 2A is a pair of diagrams. The upper diagram is a flow cytometric histogram showing that HVEM:Fc fusion protein binding to activated II-23.D7 cells is competed by $LT\beta R$:Fc fusion protein. The lower diagram is a line graph showing dose-dependent inhibition of HVEM:Fc fusion protein binding by $LT\beta R$:Fc fusion protein.
Figure 2B:
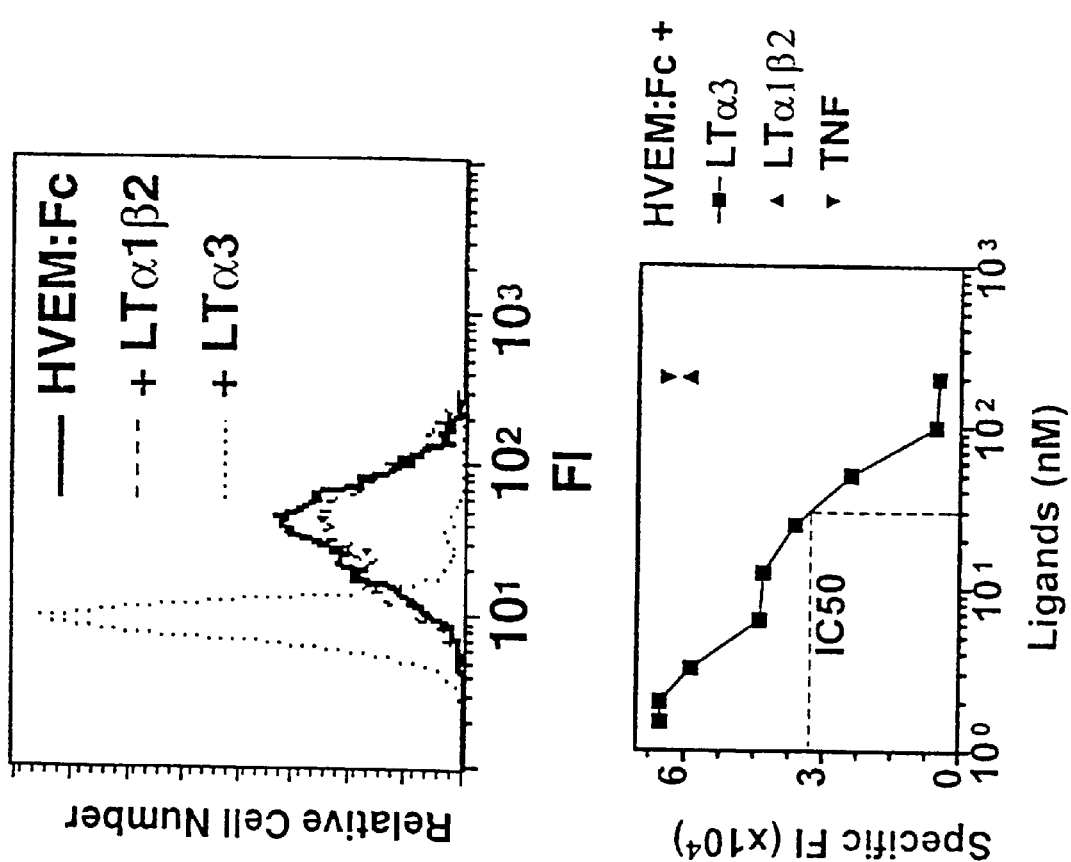
FIG. 2B is a pair of diagrams. The upper diagram is a flow cytometric histogram showing that HVEM:Fc fusion protein binding is competed by $LT\alpha$ homotrimer. The lower diagram is a line graph showing dose-dependent inhibition of HVEM:Fc fusion protein binding by the LTα homotrimer.
Figure 3:
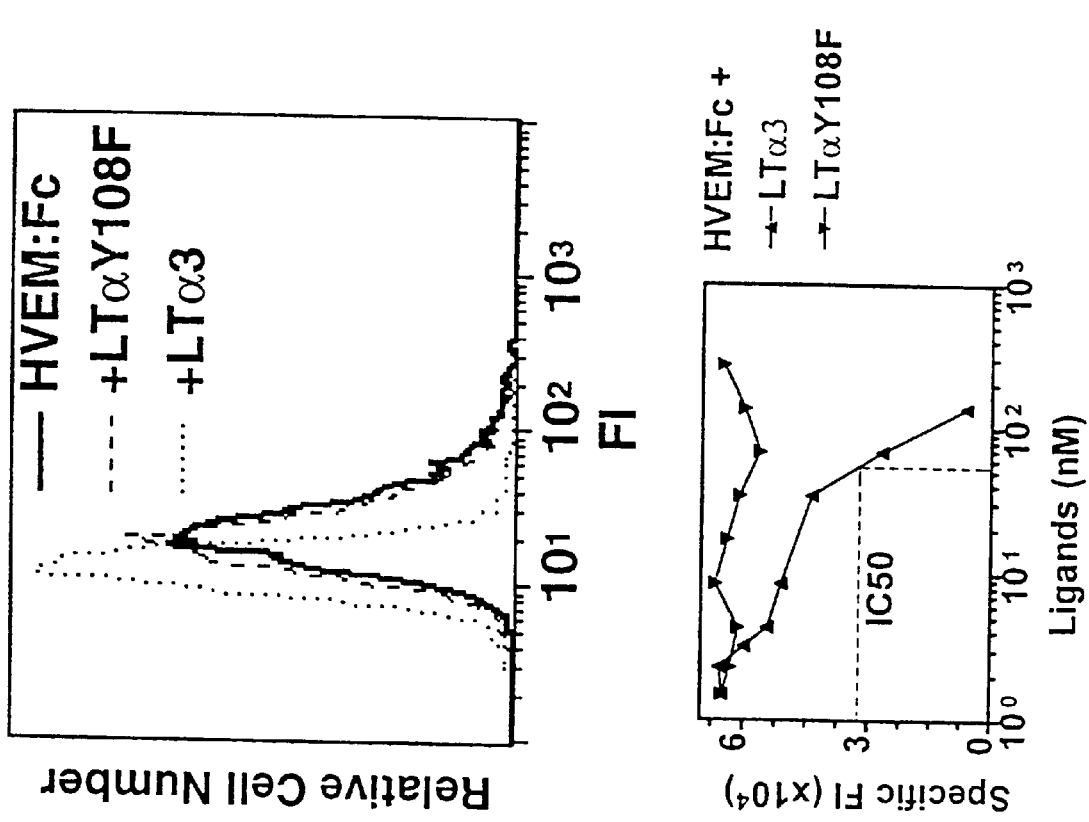
FIG. 3 is a pair of diagrams. The upper diagram is a flow cytometric histogram showing that the Tyr108Phe variant of naturally occuring LTα fails to compete for HVEM:Fc binding to II-23.D7 cells and the lower diagram is a line graph showing a LTα and LTα (Tyr108Phe) competition binding analysis.

To determine whether HVEM might bind to TNF or LTαβ complexes, LTβR:Fc and TNFR:Fc were used as competitive inhibitors of HVEM:Fc binding to II-23.D7 cells activated with PMA and ionomycin utilizing an HVEM:Fc construct with rabbit IgG Fc [Montgomery et al., cited supra]. The LTβR:Fc and HVEM:Fc (Fc of human IgG1), but not TNFR60:Fc competed for binding of HVEM:Fc (rabbit) (FIG. 2A). In addition, neither of the related receptor fusion proteins, Fas:Fc and TNFR80:Fc competed for binding of HVEM:Fc. However, surprisingly, the LTα homotrimer, but not TNF or LTα1β2 competed for HVEM:Fc binding (FIG. 2B). A TNFR60 binding mutant of LTα in which tyrosine (Tyr) at position 108 is replaced with phenylalanine (Phe) (Tyr108Phe) [Goh et al. (1991) Protein Eng. 4:785] did not compete (FIG. 3). These results indicated that the putative HVEM ligand has characteristics in common with LTαβ heterotrimers and LTα, but also has features that distinguish it from LTα1β2 and TNF. Thus LTα2β1 could be a putative surface ligand recognized by HVEM:Fc, with the caveat that the HVEM binding site(s) on LTα2β1 is not the same as TNFR60. Alternatively, HVEM:Fc might recognize a novel ligand. A biochemical approach was used to distinguish between these possibilities.

Example 3

Biochemical Characterization of the HVEM Ligand

Methods

SDS-PAGE analysis II-23.D7 cells activated for 2.5 hours with PMA or PMA and ionomycin (as in Example 1), washed twice with phosphate buffered saline (PBS), once with cysteine-methionine deficient RPMI and then resuspended in this medium containing 10% dialyzed FBS, 250 µCi each of $^{35}$S-methionine and $^{35}$S-cysteine, and activating agents for 1.5 hours. The culture supernatants were harvested and the cells lysed in buffer containing 2% NP40, HEPES pH7.0, 20 mM EDTA, 150 mM NaCl with leupeptin and aprotinin (at 10 µg/ml), PMSF (1 mM) and iodoacetamide (20 mM). The extract was precleared with human IgG (10 µg), where indicated, anti-LT antibodies and protein G beads. The receptor:Fc fusion proteins (10 µg/ml) were then added to the samples and precipitated with protein G beads. Labeled proteins were analyzed by reducing SDS-PAGE and phosphoimage (pixel range 6–200).

Cellular extracts prepared as in the above paragraph were first precleared with 10 µg of mouse IgG or monoclonal antibodies to LTα or LTβ and then HVEM:Fc was added to precipitate ligands. The proteins bound to HVEM:Fc were then resolved by reducing SDS-PAGE and detected by phosphoimage. Purification of HVEM ligand, p30 II-23.D7 cells were activated with PMA (100 ng/ml) or PMA and ionomycin (1 µg/ml) for 2.5 hours, followed by labeling with $^{35}$S-methionine and -cysteine as in the above two paragraphs. Cell extracts were precleared with human IgG (5 µg) and protein G beads to remove nonspecifically binding proteins. The extract was then depleted of LTα by treatment of the extract with TNFR60:Fc and protein G beads. HVEM:Fc and protein G beads were then added to the extract and incubated. In each case, the beads were washed three times to remove the contaminating proteins in the non-bound fraction. The beads were eluted in buffer containing 8M urea and analyzed in the first dimension by isoelectric focusing (gradient formed with an ampholine mixture of pI of 5–7 (50%0, 3–10 (40%), 2–11 (10%) and reducing SDS-PAGE (15% gel) in the second dimension.

The purification of p30 by HVEM:Fc was monitored by comparison to samples purified by LTβR:Fc or TNFR60:Fc. LTβR:Fc purified proteins, LTα1β2, were isolated from II-23.D7 cells stimulated with PMA is shown in FIG. 4A and proteins bound to TNFR60:Fc that was used to deplete LTα from the extract is shown in FIG. 4B. p30 purified by HVEM:Fc as described above is shown in FIG. 4C.

Shown in the first lane of each gel are $^{14}$C-labeled molecular weight markers and in the second lane are the receptor:Fc bound proteins run in the second dimension only.

Results

LTα is secreted by II23.D7 cells after activation with PMA [Ware et al. (1992), cited supra; Crowe et al. (1994) Science 264:707]. HVEM:Fc and TNFR:Fc precipitated secreted LTα from II-23.D7 cells stimulated with PMA and ionomycin as indicated by SDS-PAGE. LTα migrates as a range of molecular weights due to heterogeneity in glycosylation [Browning et al. (1991), cited supra]. TNFR60:Fc, but not HVEM:Fc also precipitated TNF (17 kDa, thereby confirming the results of the competition studies described supra. LTβR:Fc, as expected, did not bind any secreted proteins, but precipitated the LTβ (33 kDa) and LTα (23–25 kDa) complex from detergent extracts of PMA activated II-23.D7 cells. However, when the stimulus included ionomycin and PMA, LTβR:Fc precipitated a major band at 30 kDa, as well as a small amount of LTβ at 33 kDa and LTα at 23–25 kDa. TNFR60:Fc precipitated a 23 kDa protein identical in size to the LTα precursor. By contrast, HVEM:Fc precipitated both the 30 kDa and 23 kDa proteins. Three different receptor blocking monoclonal antibodies to LTβ failed to remove the 30 kDa protein from the extract prior to the addition of HVEM:Fc indicating that the p30 protein is antigenically unrelated to LTβ. However, anti-LTα antibodies removed the 23 kDa band from the extracts indicating relatedness of it to LTα. The inability of LTα antibodies to preclear both the 30 kDa and 23 kDa bands demonstrate that these proteins are not associated with each other, unlike LTα and LTβ which form heterotrimers [Androlewicz et al., cited supra].

p30 was purified from II-23.D7 cells by affinity chromatography. Successive TNFR60:Fc and HVEM:Fc steps were used, such that LTα is removed from the extracts by TNFR60 and thus does not interfere with p30 binding to HVEM:Fc. Two- dimensional (2D) electrophoresis of proteins that bind HVEM:Fc, TNFR60:Fc or murine LTPR:Fc revealed that p30 has a distinct charge-to-mass ratio when compared to LTα and LTβ. LTβ in the LTα1β2 complex precipitated by LTβR:Fc is acidic with four distinct charge isomers ranging in pI from 5–6.5 with a detectable increase in mass of the acidic forms (FIG. 4A). LTα, as a complex with LTβ or the LTα homotrimer bound to TNFR60 (FIG. 4B), has seven distinct isomers ranging in pI from 7–8.5; the 23 kDa LTα precursor has the most basic pI (>or=9). The pI of LTα without signal sequence is 8.9. These results are characteristic of glycosylation adducts and agree fully with previously published studies for LTα and LTβ [Browning et al. (1991), cited supra]. By contrast, p30 migrates as a broad band (pI 7–8.5) that under lower intensity resolves into three bands (FIG. 4C). The charge heterogeneity with no discernable change in mass of p30 is possibly the result of post-translational modification such as addition of phosphates or phospholipids. These results clearly demonstrate that HVEM binds a novel cell surface protein of 30 kDa with isomers of pI 7–8.5 (referred to as p30 or HVEM ligand) that is antigenically and physically distinct from LTβ. The HVEM ligand is also recognized by LTβR:Fc, but not TNFR.

Example 4

HSV gD Envelope Glycoprotein Competes With the Endogenous HVEM Ligand (p30) for Binding to HVEM:Fc Methods HVEM:Fc (2 μg/ml) was pre-incubated for 30 minutes at 4° C. with gD-1 (250 μg/ml) or gD-1 (Δ290–299) (100 μg/ml), and then added to PMA and ionomycin activated II-23.D7 cells (as in Example 1). Background staining was determined with huIgG and is equal to HVEM:Fc+gD-1 (Δ290–299). Binding of HVEM:Fc to activated II-23.D7 cells was competed with graded concentrations of gD-1 or gD-1 (Δ290–299) as in Example 1.

Results

Figure 5:
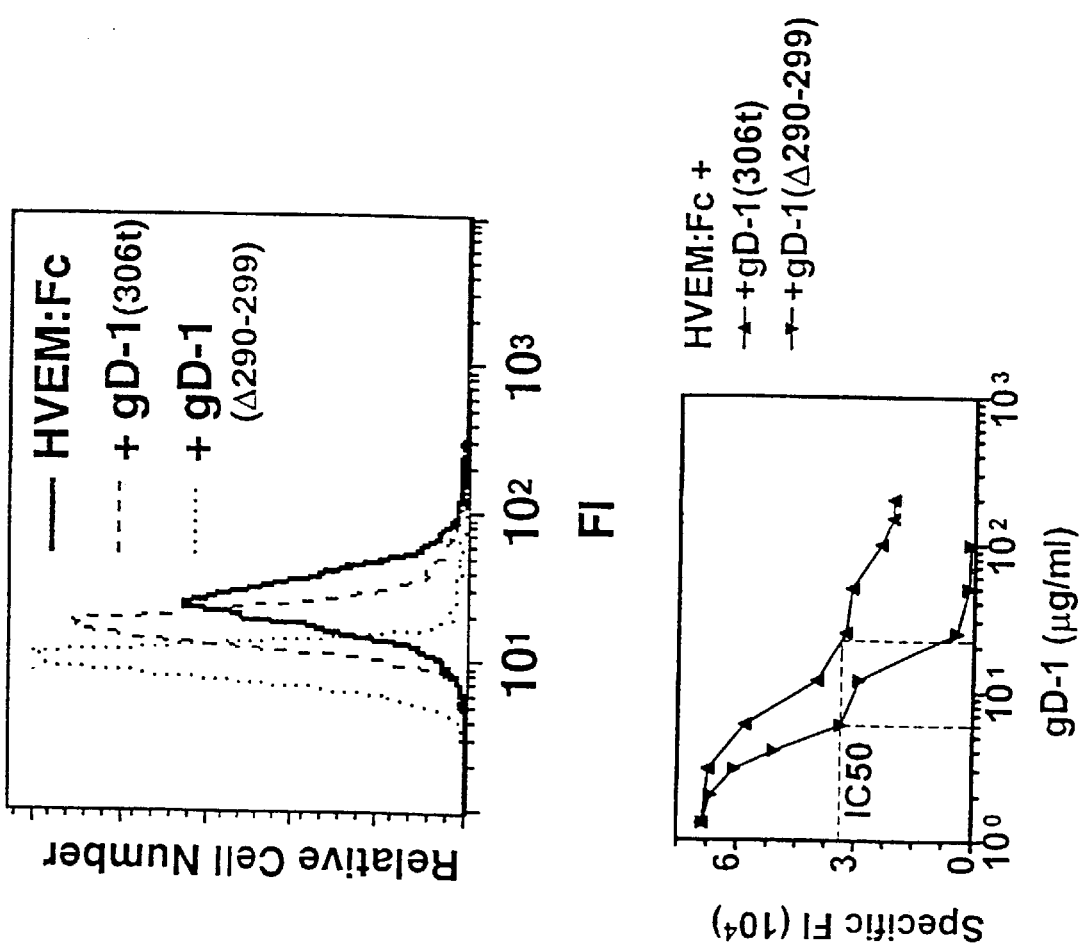
FIG. 5 is a pair or diagrams. The upper diagram is a flow cytometric histogram showing that HVEM:Fc fusion protein binding is competed by HSV gD-1 glycoprotein. The lower diagram is a line graph showing dose-dependent inhibition of HVEM:Fc fusion protein binding by HSV gD-1 glycoprotein.

The possibility that HSV gD might function as an antagonist of the HVEM cellular ligands was suggested by the binding of HSV gD-1 protein to HVEM. Soluble gD-1 and a mutant of gD, gD-1 (Δ290–299t) with enhanced binding for HVEM, were both effective at blocking HVEM binding to the surface of activated II-23.D7 cells (FIG. 5A). The effective inhibitory concentration of the gD-1 proteins correlated with their affinity for HVEM (FIG. 5B). The binding of LTβR:Fc or TNFR60:Fc to PMA or PMA/ionomycin activated II-23.D7 cells was not inhibited by gD-1 (Δ290–299t) indicating that the HVEM:gD-1 interaction is highly specific. This result suggests that gD-1 has co-evolved specifically for binding to HVEM, even though HVEM binds to ligands that are recognized by TNFR60 and LTβR. These results indicate that gD-1 is a membrane-anchored virokine of the lymphotoxins and may modulate HVEM signaling activities during entry or egress of HSV from the infected cell.

Example 5

Ligation of HVEM Results in Lymphocyte Activation

Methods

T cell activation Freshly isolated peripheral blood lymphocytes were incubated in medium containing graded dilutions of rabbit anti-HVEM or pre-immune sera [Montgomery et al., cited supra) and PMA at a submitogenic dose (1 μg/ml). Proliferation was measured after 3 days by incorporation of $^3$H-thymidine into DNA as assessed by β-scintillation counting.

Freshly isolated peripheral blood lymphocytes were activated with phytohemagglutinin (PHA) at 5 μg/ml and cultured in medium with IL-2. After 17 days the cells were restimulated with graded dilutions of anti-HVEM antiserum and anti-CD3 (OKT3) antibody at a sub-mitogenic concentration (1.5 μg/ml). Proliferation was measured after 3 days as above. B cell flow cytometric analysis Human lymphoblastoid RAJI cells were subjected to flow cytometric analysis by incubation with anti-HVEM antiserum (1:100 dilution) or control rabbit IgG at 4° C. and the stained with goat anti-rabbit IgG conjugated with phycoerythrin. $10^4$ cells were analyzed for each histogram. B cell activation RAJI was transferred into medium containing 2% FBS for 24 hours and then incubated for 3 days in the presence of the indicated dilutions of rabbit anti-HVEM antibody or medium alone. Cell proliferation was assessed as described above.

Results

Figure 6:
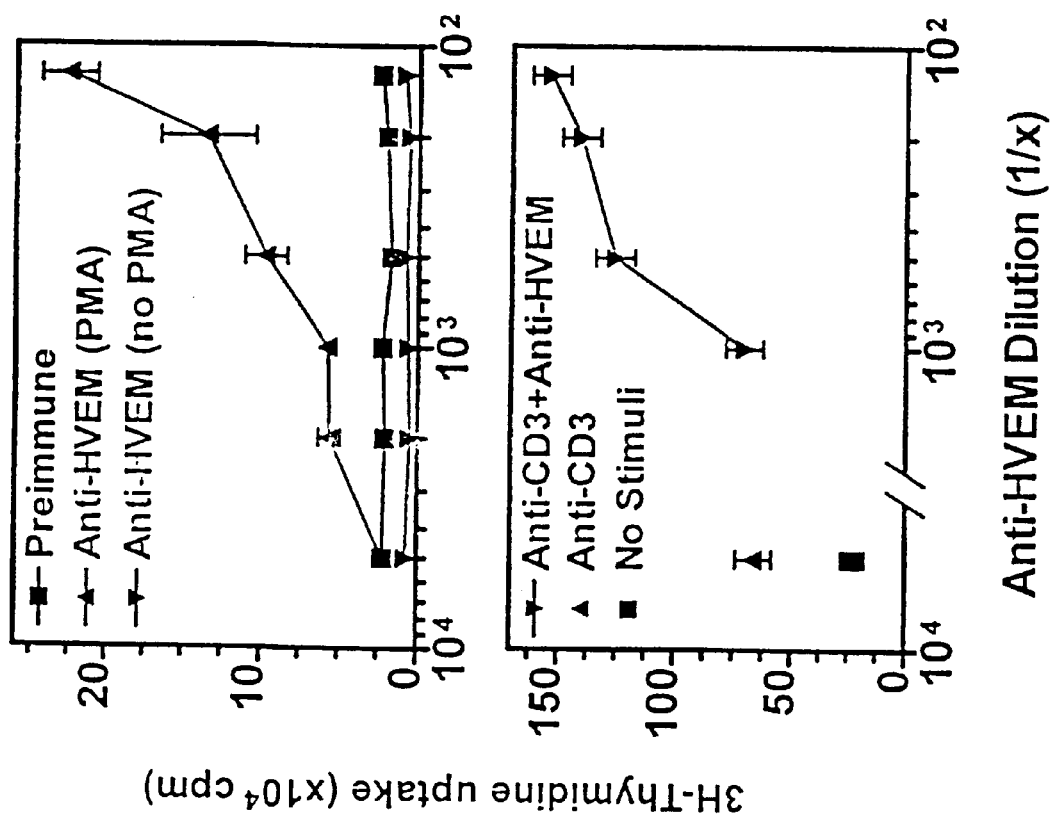
FIG. 6 is a pair of line graphs showing that anti-HVEM antibody stimulates dose-dependent proliferation in freshly isolated peripheral blood T cells (upper line graph) and memory T cells (lower line graph).

HVEM is expressed on resting CD4+T cells suggesting that it could function as a costimulatory molecule for cellular proliferation during the initial phase of an immune response. At suboptimal concentrations of PMA, anti-HVEM antibody promoted the enhanced proliferation of peripheral blood lymphocytes indicated by an increase in the uptake of $^3$H-thymidine measured after 3 days in culture (FIG. 6A). Memory lymphocytes, generated by continued culture for 10–17 days after activation with PHA, were also reactivated with anti-HVEM antibody at suboptimal concentrations of anti-CD3 antibody (FIG. 6B). This result indicated that HVEM functions in the effector phase of the immune response. Because antibodies mimic the action of TNF-related ligands [Engelmann et al. (1990) J. Biol. Chem. 265:14497], these results indicate that the cell-associated 30 kDa HVEM ligand may function as a proliferation-inducing signal for T cells.

Figure 7:
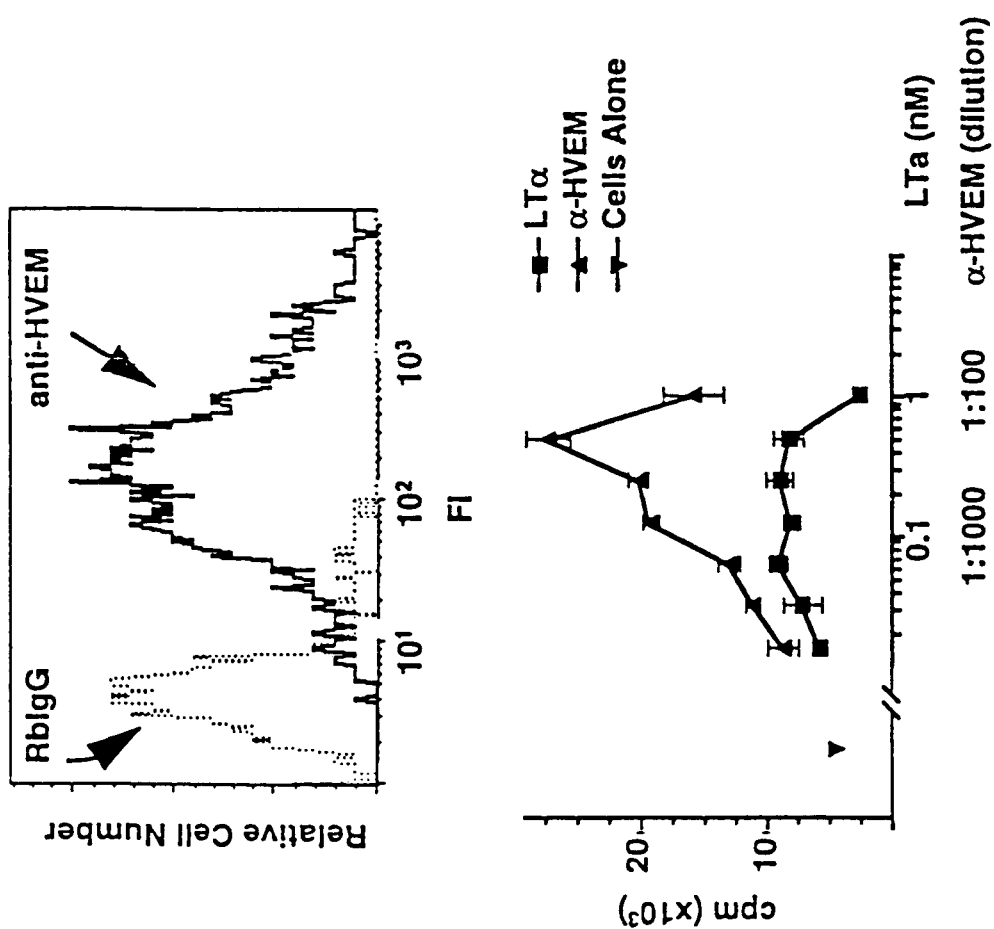
FIG. 7 is a pair of diagrams. The upper diagram is a flow cytometric histogram showing expression of HVEM on RAJI lymphoblastoid cells. The lower diagram is a line graph showing the dose-dependent proliferation of RAJI cells in response to anti-HVEM antibody.

LTα has previously been shown to stimulate growth enhancing activities for B lymphocytes including Epstein-Barr virus transformed cell lines [Abken et al. (1992) J. Immunol. 149:2785; Estrov et al. (1993) J. Exp. Med. 177:76; Kehrl et al. (1987) Science 238:1144; Gibbons et al. (1994) Eur. J. Immunol. 24:1879]. HVEM is also expressed on B lymphoblastoid lines (FIG. 7A). Anti-HVEM antibody when added to cultures of RAJI B cell lines in medium with 2% serum stimulated the uptake of $^3$H-thymidine in a dose-dependent fashion indicating that HVEM can signal maintenance of B cell viability in low serum (FIG. 7B). LTα exhibited a 2 to 3 fold stimulatory effect in this assay. The presence of TNFR60 and TNFR80 as negative growth factors may contribute a low response to LTα. The positive effect of anti-HVEM antibody may be a property unique to the p30 HVEM ligand.

Although the invention has been described with reference to the presently preferred embodiment, it should be understood that various modifications can be made without departing from the spirit of the invention. Accordingly, the invention is limited only by the following claims.

What is claimed is:

1. A substantially pure polypeptide characterized by:
   a) having an apparent molecular weight of about 30 kDa as determined by reducing SDS-PAGE;
   b) having a pI of about 7 to 8.5; and
   c) when present in a 2% NP 40, pH 7.0, 150 mM NaCl detergent extract binds to a herpes virus entry mediator (HVEM) polypeptide or
   a lymphotoxin β receptor (LTβR) polypeptide.

2. A substantially pure p30 polypeptide having an apparent molecular weight of about 30 kDa and an isoelectric charge (pI) of between about pI 7 to about pI 8.5, wherein the polypeptide, when present in a detergent extract of human T cells, comprises a composition that binds an HSV entry mediator (HVEM) protein and a lymphotoxin beta receptor (LTβR).

3. The substantially pure p30 polypeptide of claim 2, wherein the T cell is activated with phorbol myristate acetate (PMA).

4. The substantially pure p30 polypeptide of claim 2, wherein the T cell is activated with phorbol myristate acetate (PMA) and ionomycin.

5. The substantially pure p30 polypeptide of claim 2, wherein the T cell is a CD4+T cell.

6. The substantially pure p30 polypeptide of claim 5, wherein the human CD4+T cell is a II-23.D7 human T cell hybridoma.

7. The substantially pure p30 polypeptide of claim 2, wherein the p30 polypeptide at a lower isoelectric charge intensity resolves into three bands with no discernable change in 30 kDa mass between a pI of about 7 to a pI of about 8.5.

8. The substantially pure p30 polypeptide of claim 2, wherein the detergent extract is a 2% NP 40, pH 7.0, 150 mM NaCl buffered detergent extract.

9. A substantially pure isomer of the isoelectric focused, charge-resolved p30 polypeptide as set forth in claim 7.

10. A substantially pure p30 polypeptide that is substantially free of other proteins, lipids, carbohydrates and other materials with which it is naturally associated comprising the following properties:
   (a) (i) when purified by reducing SDS-PAGE gel the polypeptide is substantially only present in a single gel band of about 30 kDa, or
   (ii) when purified by isoelectric focusing gel the polypeptide is substantially only present in the gel between a pI of about 7 to a pI of about 8.5; and
   (b) when present in a detergent extract of human T cells the polypeptide binds an HSV entry mediator (HVEM) protein and a lymphotoxin beta receptor (LTβR).

11. A substantially pure p30 polypeptide purified by the following process:
   (i) providing a detergent extract of activated human CD4+T cells,
   (ii) reacting the extract with a composition comprising a 55 to 60 kDa TNF receptor (TNFR60) and removing the detergent extract-reacted TNF receptor,
   (iii) reacting the extract removed of extract-reacted TNF receptor in step (ii) with a composition comprising an HSV entry mediator protein and removing the detergent extract-reacted HSV entry mediator protein, and
   (iv) treating the detergent extract-reacted HSV entry mediator protein of step (iii) with electrophoresis and purifying the protein migrating at a molecular weight of about 30 kDa as determined by reducing SDS-PAGE.

12. The polypeptide of claim 11 further isolated by isoelectric focusing, wherein the polypeptide has a charge heterogeneity between a pI of about 7 to a pI of about 8.5.

13. A substantially pure p30 polypeptide that is substantially free of other proteins, lipids, carbohydrates and other materials with which it is naturally associated purified by the following process:
   (i) providing detergent extract of an activated human CD4+T cells,
   (ii) reacting the extract with a composition comprising a 55 to 60 kDa TNF receptor (TNFR60) and removing the detergent extract-reacted TNF receptor,
   (iii) reacting the extract removed of extract-reacted TNF receptor in step (ii) with a composition comprising an HSV entry mediator protein and purifying an HSV entry mediator protein-p30 polypeptide complex.

14. The substantially pure p30 polypeptide of claim 13, wherein the p30 polypeptide is further purified by reacting the HSV entry mediator protein-p30 polypeptide complex with 8 M urea and purifying the p30 polypeptide by gel chromatography.

* * * * *